United States Patent [19]

Herrington et al.

[11] Patent Number: 4,618,723

[45] Date of Patent: Oct. 21, 1986

[54] REDUCTION OF CARBON OXIDES WITH HYDROGEN SULFIDE

[75] Inventors: Daniel R. Herrington, Bainbridge; Philip L. Kuch, Aurora, both of Ohio

[73] Assignee: The Standard Oil Company, Cleveland, Ohio

[21] Appl. No.: 448,466

[22] Filed: Dec. 10, 1982

[51] Int. Cl.$^4$ ............... C07C 149/06; C07C 1/04; C07C 1/12; C07C 29/15

[52] U.S. Cl. ................. 568/70; 518/713; 518/715; 585/638; 585/733

[58] Field of Search ............... 568/70; 585/638, 640, 585/733; 518/713, 715

[56] References Cited

U.S. PATENT DOCUMENTS

| | | | |
|---|---|---|---|
| 2,717,260 | 9/1955 | Davis et al. | 585/638 |
| 3,070,632 | 12/1962 | Olin et al. | 568/70 |
| 4,398,050 | 8/1983 | Hofstadt et al. | 585/640 |

OTHER PUBLICATIONS

Journal of Catalysis, 49, 379 (1977), Fukuda et al.
Bulletin of Chemistry for Japan, 51, 150 (1978), Fukuda et al.
J. Chem. Soc., (1933), 145, C. E. Bawn.
Combustion and Flame, C. F. Cullis et al, 18, 225 (1972).
J. of Catalysis, 56, 407 (1979) Herman et al.
Ind. Eng. Chem. Prod. Res. Dev., 20, 87 (1981), Baglin et al.
J. Chem. Soc., Chem. Commun., 955 (1982), Ferkul et al.
J.C.S. Chem. Comm., 1114 (1981), Okuhara et al.
Transcripts of the Faraday Soc., 61, (508), 681 (1965), M. Sharma.
J. of Catalysis, 62, 84 (1980), Akimoto et al.

*Primary Examiner*—Donald G. Daus
*Assistant Examiner*—Mary E. Ceperley
*Attorney, Agent, or Firm*—S. E. McKinney; J. G. Curatolo; L. W. Evans

[57] ABSTRACT

Carbon monoxide and carbon dioxide are upgraded to valuable organic compounds, such as methanol, methane, propylene, and the like, by a thermochemical process comprising:

(a) contacting the carbon monoxide and/or carbon dioxide with hydrogen sulfide to form carbonyl sulfide, (b) contacting the carbonyl sulfide with oxygen to form carbon monoxide and sulfur dioxide, and (c) hydrogenating at least one of carbon monoxide and carbonyl sulfide to the desired organic compound.

21 Claims, 6 Drawing Figures

REDUCTION OF CARBON OXIDES WITH HYDROGEN SULFIDE

BACKGROUND OF THE INVENTION

1. Field of the Invention

This invention relates to the reduction of carbon oxides. In one aspect, the invention relates to the reduction of carbon monoxide and/or carbon dioxide with hydrogen sulfide while in another aspect, the invention relates to the upgrading of these carbon oxides to organic compounds. In yet another aspect, the invention relates to various thermochemical cycles useful for this upgrading and which employ carbonyl sulfide as a reaction intermediate.

2. Description of the Prior Art

As petroleum and natural gas reserves are continually depleted, the incentive to find alternate sources of fuels and chemicals continually increases. Many studies have been made on the hydrogenation of carbon monoxide and/or carbon dioxide to organic compounds, e.g. alkanes, alcohols, alkenes, etc., but a common drawback to these studies is the requirement for large quantities of molecular hydrogen. This requirement adds considerable expense to the proposed processes and when alkanes, alkenes and higher alcohols are the desired products, part of the valuable hydrogen is wasted in the form of by-product water. As a consequence, there continues a search for alternative ways of upgrading the carbon oxides by hydrogenation to various organic compounds.

SUMMARY OF THE INVENTION

According to this invention, carbon monoxide and/or carbon dioxide are upgraded to valuable organic compounds through the use of various thermochemical cycles which generate hydrogen in situ from hydrogen sulfide. Broadly described, the method comprises:
- (a) contacting at least one of carbon monoxide and carbon dioxide with hydrogen sulfide to form carbonyl sulfide,
- (b) contacting the carbonyl sulfide produced in (a) with oxygen to form carbon monoxide and sulfur dioxide, and
- (c) hydrogenating at least one of carbon monoxide and carbonyl sulfide to form an organic compound.

These thermochemical cycles can be divided into three broad categories: carbon monoxide reduction, carbon dioxide reduction and combined carbon monoxide/carbon dioxide reduction. Each of these categories can be subdivided into groups of two or three cycles each. All of the thermochemical cycles contain at least three steps and some contain four steps. In each of these cycles, the sulfur from hydrogen sulfide is converted into sulfur dioxide which can be used in the production of sulfuric acid or elemental sulfur. Although generated within the cycles, molecular hydrogen is not required as a feedstock and thus there is no net hydrogen consumption.

DETAILED DESCRIPTION OF THE INVENTION

Overview

Figure 1:
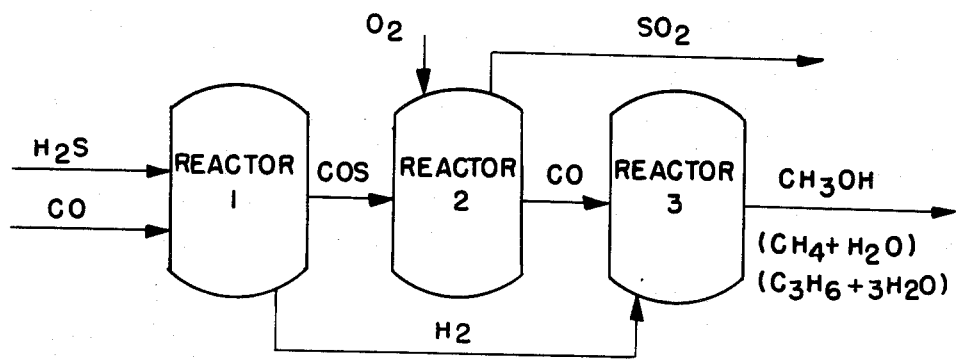
FIG. 1 is a schematic flow diagram describing one method for reducing carbon monoxide.

Although this invention encompasses a multitude of various thermochemical cycles, these cycles are built from seven basic reactions. However, some of these reactions can yield various product mixes depending upon such variables as reactant stoichiometry, catalysts, process conditions, etc.

All these cycles start with one of three reactions: the reduction of carbon monoxide, the reduction of carbon dioxide, or the concurrent reduction of carbon monoxide and carbon dioxide. In each reaction, the reducing agent is hydrogen sulfide.

The one reaction common to all cycles is the oxidation of carbonyl sulfide to carbon monoxide and sulfur dioxide. This reaction is generally the second step in the various cycle sequences but occasionally it is the third or fourth step.

The concluding reactions involve the hydrogenation of either carbon monoxide or carbonyl sulfide. The reducing agent in these reactions is either hydrogen sulfide or hydrogen and the products are organic compounds except for the reaction of carbon monoxide and hydrogen sulfide which produces carbonyl sulfide and hydrogen.

The hallmark of this invention is not in the individual reactions but in their combination into an overall scheme for upgrading carbon monoxide and dioxide with hydrogen sulfide generally and the various thermochemical cycles specifically. As noted earlier, these cycles do not require hydrogen as a feedstock and employ abundant, relatively inexpensive reactants. Moreover, these cycles provide convenient routes to a myriad of organic compounds.

The Periodic Table here referenced is that published in the *Handbook of Chemistry and Physics*, 61 Ed., CRC Press (1980–81).

Carbon Monoxide Reduction

The thermochemical cycles for the reduction of carbon monoxide with hydrogen sulfide are 3-step cycles which differ from one another primarily by the definition of the third step. A first group of such cycles are described by the following three cycles:

Cycle A

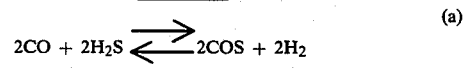
(a)

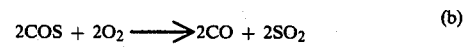
(b)

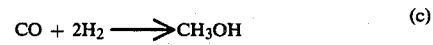
(c)

(d)

-continued

Cycle B $$3CO + 3H_2S \rightleftarrows 3COS + 3H_2 \quad (a)$$

$$3COS + 3O_2 \longrightarrow 3CO + 3SO_2 \quad (b)$$

$$CO + 3H_2 \longrightarrow CH_4 + H_2O \quad (c)$$

$$CO + 3H_2S + 3O_2 \longrightarrow CH_4 + 3SO_2 + H_2O \quad (d)$$

Cycle C $$6CO + 6H_2S \rightleftarrows 6COS + 6H_2 \quad (a)$$

$$6COS + 6O_2 \longrightarrow 6CO + 6SO_2 \quad (b)$$

$$3CO + 6H_2 \longrightarrow C_3H_6 + 3H_2O \quad (c)$$

$$3CO + 6H_2S + 6O_2 \longrightarrow C_3H_6 + 6SO_2 + 3H_2O \quad (d)$$

The first step of each cycle is the reaction of carbon monoxide with hydrogen sulfide to form carbonyl sulfide and hydrogen. This is a known vapor phase reaction and is described in such articles as *Journal of Catalysis*, 49, 379 (1977) and *Bulletin of Chemistry for Japan*, 51, 150 (1978), both by Fukuda et al. The reaction is typically conducted within a temperature range of 200°–600° C., preferably 250°–400° C., and within a pressure range of 0–1,000 psig, preferably 0–500 psig. Stoichiometric amounts of reactants are required although preferably an excess of one of the reactants, preferably hydrogen sulfide, is present as a means of shifting the equilibrium to the right. Preferably this reaction is conducted in the presence of a catalyst which is typically an oxide or sulfide of a Group 6b or 8 metal of the Periodic Table and optionally promoted with one or more metal compounds from Groups 4a, 1b and 2a. These catalysts can be supported or unsupported and if supported, the support can be selected from a wide range of materials including such compounds as alumina, silica, silica-alumina, zirconium oxide, thorium oxide, titanium oxide, etc. The catalyst can take any convenient physical shape including tablets, spheres, pellets, extrusions, powder, etc., and when used in combination with a support can be either impregnated or coated. This reaction can be conducted in any vapor-phase reactor including the various fixed- and fluid-bed configurations and the contact time of the reactants over the catalyst bed will vary with the other process parameters. Typically, a contact time of 1–20, preferably 2–10, seconds is employed.

The second reaction in these cycles is the oxidation of carbonyl sulfide to carbon monoxide and sulfur dioxide. Again, this is a known reaction and is described in such articles as *Journal of the Chemical Society*, Bawn, C. E. H., 1933, 145 and *Combustion and Flame*, Cullis, C. F. and Mulcahy, M. F. R., 18, 225 (1972). This is a combustion reaction which proceeds well in the absence of a catalyst. However, a catalyst, such as quartz chips, can be employed to promote smooth combustion, high conversions and/or good selectivities.

The reaction of carbonyl sulfide with oxygen is a vapor-phase reaction and is typically conducted at a temperature range of about 200°–500° C., preferably about 250°–350° C. and at a pressure of about 0–1,000 psig, preferably about 0–500 psig. Stoichiometric amounts of oxygen and carbonyl sulfide are required and since this reaction is not equilibrium limited, little if any benefit is gained from having one of the reactants present in an excess. Contact time will vary with the process conditions but typically in a fixed-bed reactor a contact time between about 1 and about 20, preferably between about 2 and about 10, seconds is used.

The third reaction in these cycles is the hydrogenation of carbon monoxide to one or more organic products. The organic compounds produced by this reaction will depend upon a number of factors including the reactant stoichiometry, reaction conditions and the nature of the catalysts. For example, in Cycle A methanol is produced when two moles of hydrogen are reacted with one mole of carbon monoxide in the presence of a supported copper-zinc oxide (*Journal of Catalysis*, Herman et al., 56, 407 (1979)) or thorium-copper intermetallic (*Ind. Eng. Chem. Prod. Res. Dev.*, Baglin et al., 20 87 (1981)) catalyst while in Cycle B methane is produced when three moles of hydrogen are reacted at low pressure with carbon monoxide in the presence of a supported ruthenium catalyst (*J. Chem. Soc., Chem. Commun.*, Ferkul et al., 955 L (1982)). Propylene is produced by this reaction in Cycle C when two moles of hydrogen are reacted at an elevated pressure with one mole of carbon monoxide in the presence of a supported, highly dispersed potassium-promoted ruthenium catalyst (*J.C.S. Chem. Comm.*, Okuhara et al., 1114 (1981)). Other organic compounds may be produced as by-products of these reactions or if other catalysts and/or conditions are used, an entirely different product mix may be obtained, such as a mixture of alcohols, Fischer-Tropsch hydrocarbons, or mixed olefins.

FIG. 1 shows how these three reactions can be integrated into a continuous process. Hydrogen sulfide and carbon monoxide are fed to a first reactor which produces carbonyl sulfide and hydrogen. The carbonyl sulfide is passed to a second reactor where it is contacted with oxygen to form carbon monoxide and sulfur dioxide. The sulfur dioxide is recovered as a by-product and the carbon monoxide is fed to a third reactor with the hydrogen produced in the first reactor. The organic compounds are then recovered from the third reactor.

A second group of carbon monoxide reduction cycles are illustrated by Cycles D, E and F.

Cycle D $$3CO + 3H_2S \rightleftarrows 3COS + 3H_2 \quad (a)$$

$$2COS + 2O_2 \longrightarrow 2CO + 2SO_2 \quad (b)$$

$$COS + 3H_2 \longrightarrow CH_3SH + H_2O \quad (c)$$

$$CO + 3H_2S + 2O_2 \longrightarrow CH_3SH + 2SO_2 + H_2O \quad (d)$$

Cycle E $$4CO + 4H_2S \rightleftarrows 4COS + 4H_2 \quad (a)$$

$$3COS + 3O_2 \longrightarrow 3CO + 3SO_2 \quad (b)$$

-continued $$COS + 4H_2 \longrightarrow CH_4 + H_2O + H_2S \quad (c)$$

$$CO + 3H_2S + 3O_2 \longrightarrow CH_4 + 3SO_2 + H_2O \quad (d)$$

Cycle F $$18CO + 18H_2S \rightleftarrows 18COS + 18H_2 \quad (a)$$

$$15COS + 15O_2 \longrightarrow 15CO + 15SO_2 \quad (b)$$

$$3COS + 18H_2 \longrightarrow C_3H_6 + 3H_2O + 3H_2S \quad (c)$$

$$3CO + 15H_2S + 15O_2 \longrightarrow C_3H_6 + 15SO_2 + 3H_2O \quad (d)$$

As is readily evident, these three cycles differ from Cycles A, B and C in that the third reaction in Cycles D, E and F is the hydrogenation of carbonyl sulfide to the desired organic product. Again, the products produced by this particular reaction is dependent upon the reactant stoichiometry, process conditions and the nature of the catalysts. Obviously, since carbonyl sulfide and hydrogen are the products of the first reaction in these cycles, the catalysts, conditions and/or reactant stoichiometry there used are different from those used in the third reaction. Generally, the hydrogen is present in excess of the carbonyl sulfide and the catalysts employed include supported metal oxides such as nickel oxide, cobalt oxide, etc. These reactions are typically conducted within a temperature range of 200°–500° C., preferably between 250°–350° C., and within a pressure range of 0–1,000 psig, preferably between 0–500 psig. Exemplary of these reactions is the use of a supported nickel oxide and elevated pressure (e.g. 50 atmospheres) to promote reaction (c) of Cycle D and the use of the same catalyst (supported NiO) but atmospheric pressure to promote reactions (c) of Cycles E and F. As with the reactions (c) of Cycles A, B and C, other organic compounds may be produced as by-products of these reactions or if other catalyst and/or conditions are used, then an entirely different product mix may be obtained.

Figure 2:
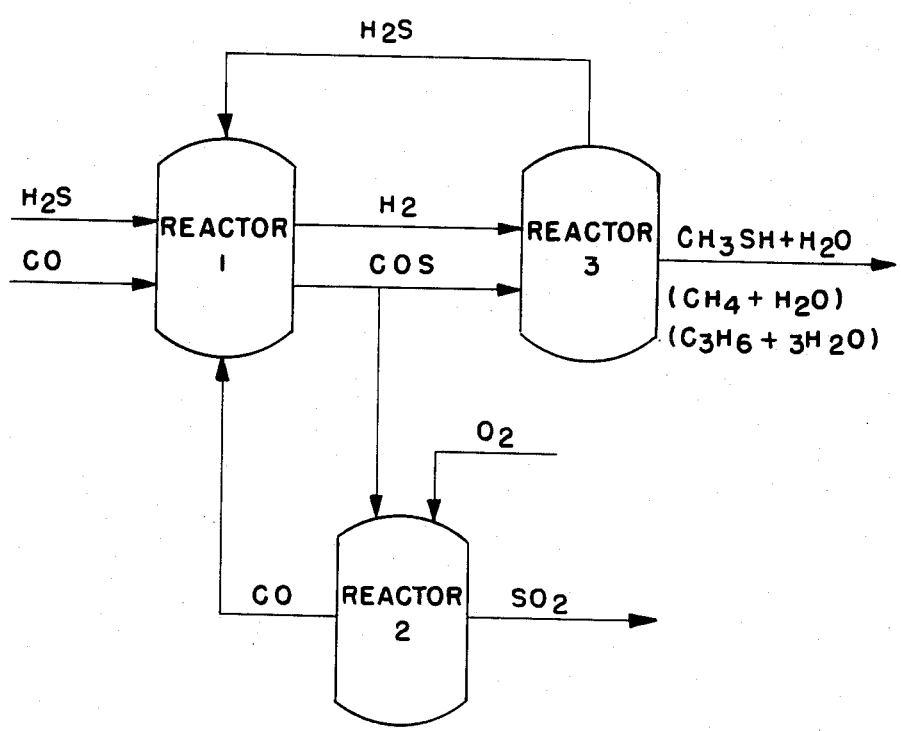
FIG. 2 is a schematic flow diagram describing another method for reducing carbon monoxide.

FIG. 2 illustrates the integration of these three individual reactions in Cycles D, E and F and combined into a continuous process. The first reactor is fed with hydrogen sulfide and carbon monoxide to produce hydrogen an carbonyl sulfide. The carbonyl sulfide product stream is split and part is fed to a second reactor where it is combusted with oxygen to produce carbon monoxide and sulfur dioxide. The sulfur dioxide is removed from the process while the carbon monoxide is recycled to the first reactor. The hydrogen is fed to a third reactor where it is reacted with the remaining carbonyl sulfide produced from the first reactor to form the desired organic product(s) and hydrogen sulfide by-product. The hydrogen sulfide is recycled to the first reactor.

Carbon Dioxide Reduction

A first group of carbon dioxide reduction cycles are described by the following three cycles:

Cycle G

-continued $$CO_2 + H_2S \rightleftarrows COS + H_2O \quad (a)$$

$$3COS + 3O_2 \longrightarrow 3CO + 3SO_2 \quad (b)$$

$$2CO + 2H_2S \rightleftarrows 2COS + 2H_2 \quad (c)$$

$$CO + 2H_2 \longrightarrow CH_3OH \quad (d)$$

$$CO_2 + 3H_2S + 3O_2 \longrightarrow CH_3OH + 3SO_2 + H_2O \quad (e)$$

Cycle H $$CO_2 + H_2S \rightleftarrows COS + H_2O \quad (a)$$

$$4COS + 4O_2 \longrightarrow 4CO + 4SO_2 \quad (b)$$

$$3CO + 3H_2S \rightleftarrows 3COS + 3H_2 \quad (c)$$

$$CO + 3H_2 \longrightarrow CH_4 + H_2O \quad (d)$$

$$CO_2 + 4H_2S + 4O_2 \longrightarrow CH_4 + 4SO_2 + 2H_2O \quad (e)$$

Cycle I $$3CO_2 + 3H_2S \rightleftarrows 3COS + 3H_2O \quad (a)$$

$$9COS + 9O_2 \longrightarrow 9CO + 9SO_2 \quad (b)$$

$$6CO + 6H_2S \rightleftarrows 6COS + 6H_2 \quad (c)$$

$$3CO + 6H_2 \longrightarrow C_3H_6 + 3H_2O \quad (d)$$

$$3CO_2 + 9H_2S + 9O_2 \longrightarrow C_3H_6 + 9SO_2 + 6H_2O \quad (e)$$

As noted earlier, this is a known reaction and it can be conducted in either the liquid or vapor phase. See *Transcripts of the Faraday Society*, M. M. Sharms, 61 (508), page 681 (1965) and *Journal of Catalysis*, Akimoto and Dalla Lana, 62, 84 (1980). Typically this reaction is conducted in the vapor phase within a temperature range of 20°–800° C., preferably between 100°–700° C. and within a pressure range of 0–3,000 psig, preferably between 0–500 psig. Since stoichiometric amounts of carbon dioxide and hydrogen sulfide are required for this reaction, the mole ratio of carbon dioxide to hydrogen sulfide is typically at least 1:1 but an excess of one of the reactants, preferably carbon dioxide, is generally fed to the reactor to shift the equilibrium to favor carbonyl sulfide production.

Although this reaction can be conducted noncatalytically, preferably the reaction is conducted in the presence of a catalyst, typically an acidic catalyst such as a Lewis or Bronsted acid. Representative of these catalysts are the oxides and/or sulfides of the Group 6b and 7b metals, optionally promoted with one or more metals or metal compounds from Groups 7b, 8, 1a, 1b, 2b, etc., of the Periodic Table. These catalysts can take any physical form, e.g. tablets, pellets, powder, extrudates, soluble (useful in homogenous liquid phase reactions), etc. and can be either supported or unsupported. Representative supports include alumina and/or silica, zirconium oxide, thorium oxide, titanium oxide, and the like. If supported, the catalyst can be either coated onto or impregnated into the support and in the case of the latter, typically such that the catalyst is present in an amount of at least one weight percent, based on the combined weight of the support and the catalyst, preferably in an amount of at least about 5 weight percent. In the case of the former, the catalyst is present in an amount of at least 5, preferably at least 15, weight percent.

When the reaction is conducted in the vapor phase, the reaction can be conducted either in a fixed- or fluid-bed mode with a contact time in the range of 0.1-20 seconds and preferably between about 1-10 seconds, the exact time dependent on such variables as catalyst composition, temperature, reactants, etc. When the reaction is conducted in the liquid phase, either a soluble or insoluble catalyst can be used with a sufficient residence time that allows the reaction to reach equilibrium. Exemplary conditions for this mode of reaction are described by M. M. Sharms, supra.

The second reaction in these cycles is the combustion of carbonyl sulfide and this has been amply described earlier. Likewise, the third and fourth reactions in these cycles have also been earlier described.

Figure 3:
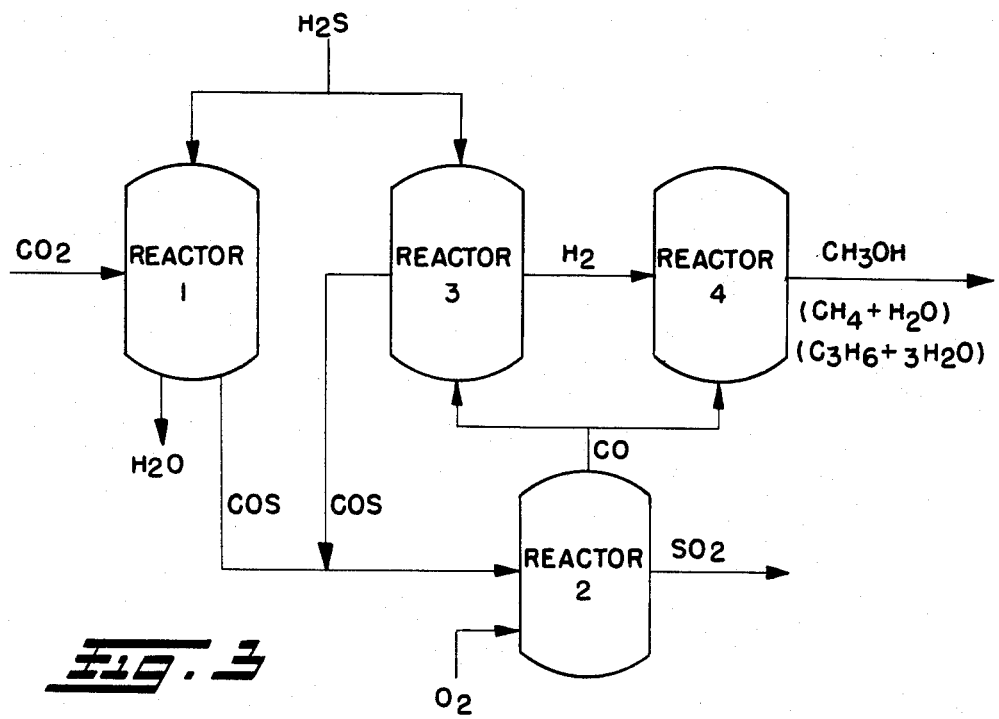
FIG. 3 is a schematic flow diagram describing one method for reducing carbon dioxide.

FIG. 3 describes a process where the four steps of Cycles G-I are integrated into a single process. Carbon dioxide is fed to a first reactor where it is reacted with hydrogen sulfide to produce water and carbonyl sulfide. The water is withdrawn from the process while the carbonyl sulfide is fed to a second reactor where it is combusted to produce sulfur dioxide and carbon monoxide. The sulfur dioxide is withdrawn from the process while the carbon monoxide is split into two streams one of which is fed to a third reactor where it is contacted with hydrogen sulfide to produce carbonyl sulfide and hydrogen and the other of which is fed to a fourth reactor where it is reacted with hydrogen. The hydrogen fed to the fourth reactor is one of the products of the third reactor while the carbonyl sulfide product of the third reactor is recycled to the second reactor. The desired organic product(s) is recovered from the fourth reactor.

A second group of carbon dioxide reduction cycles is illustrated by Cycles J, K and L. Each of the reactions in these cycles has been discussed above.

Cycle J

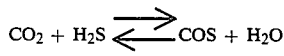 (a)

 (b)

 (c)

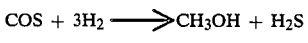 (d)

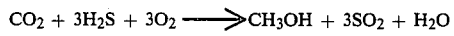 (e)

Cycle K

-continued

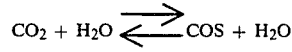 (a)

 (b)

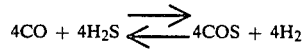 (c)

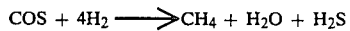 (d)

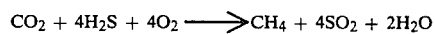 (e)

Cycle L

 (a)

 (b)

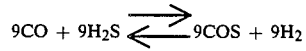 (c)

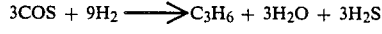 (d)

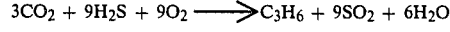 (e)

Figure 4:
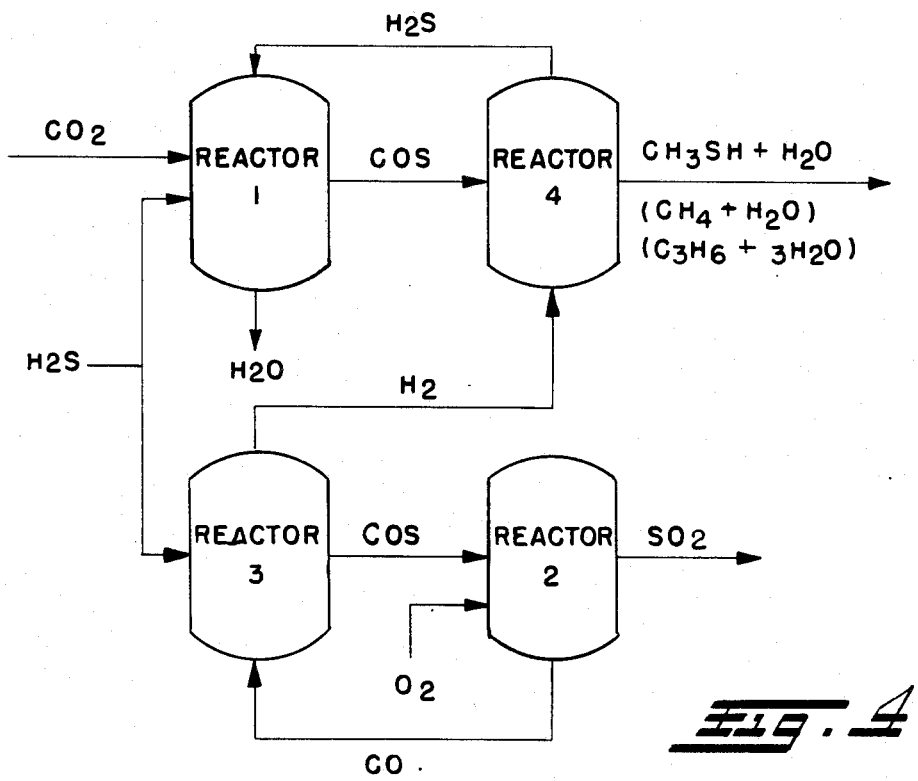
FIG. 4 is a schematic flow diagram describing another method for reducing carbon dioxide.

FIG. 4 shows the individual steps of these cycles integrated into a single process. Carbon dioxide and hydrogen sulfide are fed to a first reactor to produce carbonyl sulfide and water. The water is withdrawn from the process while the carbonyl sulfide is fed to a fourth reactor where it is hydrogenated to hydrogen sulfide and the desired organic compound(s). The hydrogen sulfide is recycled to the first reactor while the organic product(s) is removed. The hydrogen fed to the fourth reactor is a product of the reaction of hydrogen sulfide and carbon monoxide in a third reactor which also produces carbonyl sulfide. This carbonyl sulfide is fed to a second reactor where it is combusted to sulfur dioxide and carbon monoxide which is recycled to the third reactor.

Combined Carbon Monoxide/Carbon Dioxide Reduction

In one embodiment of this invention, carbon monoxide and carbon dioxide can be reduced with hydrogen sulfide in a single step. One group of such cycles is given below.

Cycle M

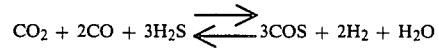 (a)

 (b)

 (c)

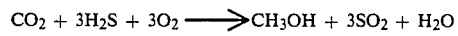 (d)

Cycle N

-continued $$CO_2 + 3CO + 4H_2S \rightleftarrows 4COS + 3H_2 + H_2O \quad (a)$$

$$4COS + 4O_2 \longrightarrow 4CO + 4SO_2 \quad (b)$$

$$CO + 3H_2 \longrightarrow CH_4 + H_2O \quad (c)$$

$$CO_2 + 4H_2S + 4O_2 \longrightarrow CH_4 + 4SO_2 + 2H_2O \quad (d)$$

Cycle O $$3CO_2 + 6CO + 9H_2S \rightleftarrows 9COS + 6H_2 + 3H_2O \quad (a)$$

$$9COS + 9O_2 \longrightarrow 9CO + 9SO_2 \quad (b)$$

$$3CO + 6H_2 \longrightarrow C_3H_6 + 3H_2O \quad (c)$$

$$3CO_2 + 9H_2S + 9O_2 \longrightarrow C_3H_6 + 9SO_2 + 6H_2O \quad (d)$$

The first reaction in each of these cycles is a vapor phase reaction and is typically conducted with a temperature range of 200°–500° C., preferably between 250°–350° C. and within a pressure range of 0–1,000 psig, preferably between 0–500 psig. Since stoichiometric amounts of reactants are required, the mole ratio of carbon dioxide to carbon monoxide to hydrogen sulfide is typically at least 1:2:1 but an excess of hydrogen sulfide is generally used to shift the equilibrium of the reaction to favor carbonyl sulfide production. This reaction is preferably conducted in the presence of a catalyst of any convenient physical form, i.e. tablets, pellets, powder, extrudates, etc., and a wide variety of catalyst compositions can be employed. Representative compositions include the oxides and/or sulfides of Group 6b and 8 of the Periodic Table and these can be supported or unsupported and optionally promoted with metals or metal compounds from Groups 2a, 1b and 4a. Representative supports for these catalysts include alumina and/or silica, zirconium oxide, thorium oxide, titanium oxide, etc. The reaction can be conducted in either a fixed or fluid-bed reactor with a contact time typically in the range of 0.1–20 seconds, preferably between about 1–10 seconds.

The second and third reactions in these cycles have been described earlier.

Figure 5:
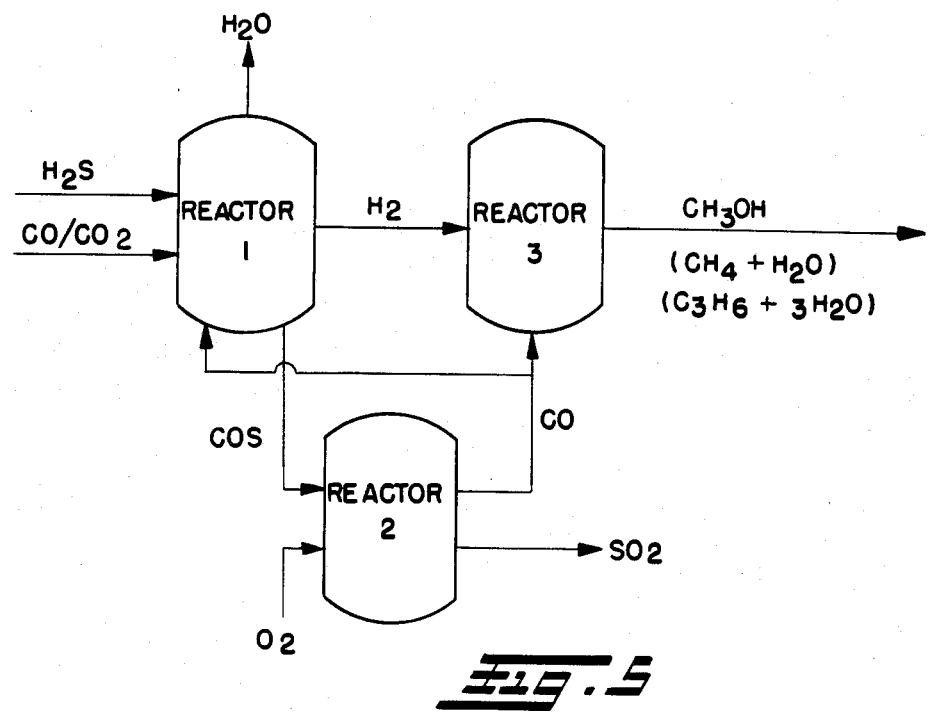
FIG. 5 is a schematic flow diagram describing one method for reducing carbon monoxide and carbon dioxide concurrently.

FIG. 5 describes how these three steps can be combined into an integrated process. Hydrogen sulfide and a feed of combined carbon monoxide and carbon dioxide is fed to a first reactor where water, hydrogen and carbonyl sulfide are produced. The water is removed from the process while the carbonyl sulfide is fed to a second reactor where it is combusted to form sulfur dioxide and carbon monoxide. The sulfur dioxide is removed from the process while the carbon monoxide is split in two streams, one of which is recycled to the first reactor while the other is fed to a third reactor where it is contacted with the hydrogen product of the first reactor to form the desired organic compound(s).

A second group of combined carbon monoxide/carbon dioxide reduction cycles are described by the Cycles P, Q and R.

Cycle P $$CO_2 + 3CO + 4H_2S \rightleftarrows 4COS + 3H_2 + H_2O \quad (a)$$

$$3COS + 3O_2 \longrightarrow 3CO + 3SO_2 \quad (b)$$

$$COS + 3H_2 \longrightarrow CH_3OH + H_2S \quad (c)$$

$$CO_2 + 4H_2S + 3O_2 \longrightarrow CH_3SH + 3SO_2 + 2H_2O \quad (d)$$

Cycle Q $$CO_2 + 4CO + 5H_2S \rightleftarrows 5COS + 4H_2 + H_2O \quad (a)$$

$$4COS + 4O_2 \longrightarrow 4CO + 4SO_2 \quad (b)$$

$$COS + 4H_2 \longrightarrow CH_4 + H_2O + H_2S \quad (c)$$

$$CO_2 + 4H_2S + 4O_2 \longrightarrow CH_4 + 4SO_2 + 2H_2O \quad (d)$$

Cycle R $$3CO_2 + 9CO + 12H_2S \rightleftarrows 12COS + 9H_2 + 3H_2O \quad (a)$$

$$9COS + 9O_2 \longrightarrow 9CO + 9SO_2 \quad (b)$$

$$3COS + 9H_2 \longrightarrow C_3H_6 + 3H_2S + 3H_2O \quad (c)$$

$$3CO_2 + 9H_2S + 9O_2 \longrightarrow C_3H_6 + 9SO_2 + 6H_2O \quad (d)$$

The individual reactions in each of these cycles has been previously described.

Figure 6:
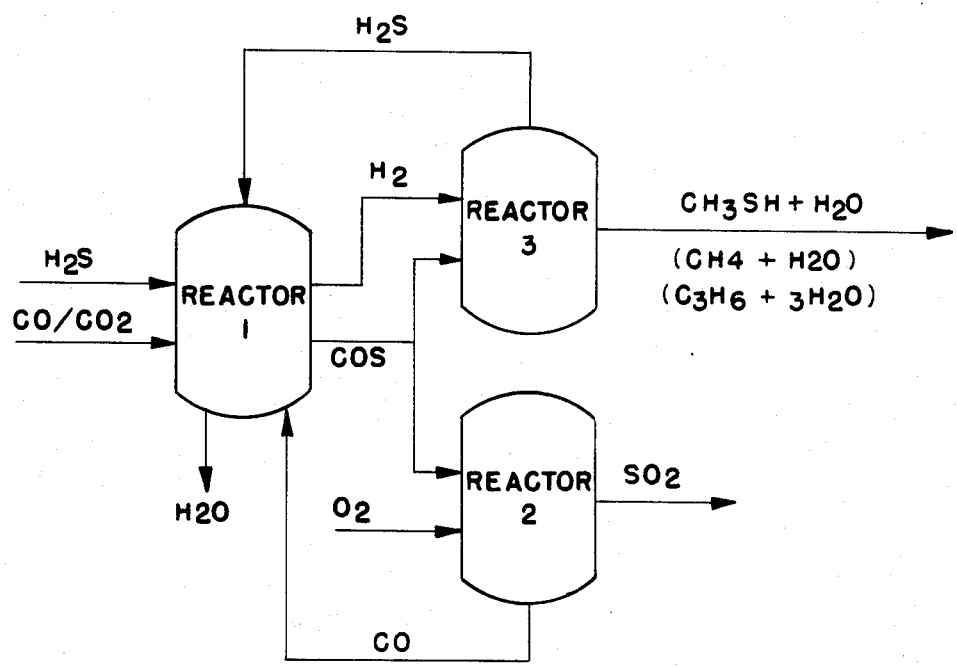
FIG. 6 is a schematic flow diagram describing another method for reducing carbon monoxide and carbon dioxide concurrently.

FIG. 6 is a description of how the steps of Cycles P, Q and R can be combined into an integrated process. Hydrogen sulfide and a combined stream of carbon monoxide and carbon dioxide are fed to a first reactor where water, carbonyl sulfide and hydrogen are produced. Water is removed from the process while the carbonyl sulfide is split into two streams, one of which is fed to a second reactor for combustion to sulfur dioxide and carbon monoxide while the other stream is fed to a third reactor to be hydrogenated to hydrogen sulfide and the desired organic compound(s). The sulfur dioxide of the second reactor is removed from the process while the carbon monoxide is recycled to the first reactor. The hydrogen sulfide produced in the third reactor is recycled to the first reactor while the organic compound(s) is recovered.

As a review of each of these cycles shows, the carbon oxides are reduced without the consumption of any added hydrogen, i.e. the required hydrogen is supplied fron hydrogen sulfide. As such, this invention as represented by the above cycles provides an efficient process for upgrading carbon oxides to valuable organic compounds using only hydrogen sulfide as the source of molecular hydrogen. The other by-products of water and sulfur dioxide are a clean disposal product and a valuable feedstock respectively (the latter for the production of sulfuric acid and elemental sulfur).

The following examples are illustrative embodiments of this invention. Unless indicated to the contrary, all parts and percentages are by weight.

SPECIFIC EMBODIMENTS

Reaction of Carbon Dioxide and Hydrogen Sulfide

Examples 1-5 describe the preparation of a catalyst used for the reaction of hydrogen sulfide and carbon dioxide.

Example 1

A 40 g sample of $\frac{1}{8}$ in. diameter Alundum ® spheres (alumina) was treated with 3.5 g $H_2O$ and rolled in a rolling mill for 30 min. Following this treatment, 10 g $CoMoO_4$ was added in four approximately equal portions, rolling 15-20 minutes after each addition. The resulting coated catalyst was dried overnight at 100° C.

1.08 g ammonium paratungstate, dried overnight at 110° C., and calcined 4 hours at 400° C.

Example 5

A 10 g sample of $\gamma$-$Al_2O_3$ was impregnated with an aqueous solution containing 3.62 g $Mn(NO_3)_2.6H_2O$, dried overnight at 110° C., and calcined 4 hours at 400° C.

In Examples 6-11, 20 cc of catalyst was placed into a quartz tube between quartz wool plugs, flushed well with nitrogen, heated to the initial run temperature under flowing nitrogen and kept under flowing nitrogen at this temperature for several hours. Following this pretreatment, hydrogen sulfide and carbon dioxide were introduced at a 1:1 molar ratio with a 10 second contact time. Following the initial run, additional runs were made at higher temperatures. The results of these runs are reported in Table I.

TABLE I

| | REACTION OF CARBON DIOXIDE AND HYDROGEN SULFIDE OVER VARIOUS CATALYSTS | | |
|---|---|---|---|
| Example No. | Catalyst | Temperature (°C.) | COS Yield (%)[1] |
| 6 | CO MO O$_4$ | 200 | — |
|  | Co Mo O$_4$ | 400 | 1.0 |
|  | Co Mo O$_4$ | 500 | 4.0 |
|  | Co Mo O$_4$ | 600 | 7.0 |
| 7 | Cs Cu$_{0.2}$ Zn$_{0.5}$ Mn$_{0.5}$ MoO$_x$/10 wt % Sn | 300 | — |
|  | Cs Cu$_{0.2}$ Zn$_{0.5}$ Mn$_{0.5}$ MoO$_x$/10 wt % Sn | 400 | 7.0 |
|  | Cs Cu$_{0.2}$ Zn$_{0.5}$ Mn$_{0.5}$ MoO$_x$/10 wt % Sn | 600 | 11.3 |
| 8 | Ag$_{0.1}$ Cu$_{0.45}$ Ni$_{0.45}$ WO$_x$ | 400 | 6.0 |
|  | Ag$_{0.1}$ Cu$_{0.45}$ Ni$_{0.45}$ WO$_x$ | 600 | 6.6 |
| 9* | Nalco 506 (NiO/MoO$_3$/Al$_2$O$_3$) | 400 | 7.0 |
|  | Nalco 506 (NiO/MoO$_3$/Al$_2$O$_3$) | 600 | 11.7 |
| 10 | Ni WO$_x$/Al$_2$O$_3$ | 400 | 6.8 |
|  | Ni WO$_x$/Al$_2$O$_3$ | 600 | 11.7 |
| 11 | Mn O$_x$/Al$_2$O$_3$ | 400 | 4.0 |
|  | Mn O$_x$/Al$_2$O$_3$ | 600 | 9.7 |

*This was a commercially purchased catalyst.
[1]Based on moles of $CO_2$ fed to reactor.

Example 2

A 30 g sample of $\gamma$-$Al_2O_3$ was stirred in the presence of 13 ml $H_2O$ containing 0.5 g $Cu(NO_3)_2.3H_2O$, 1.52 g $Zn(NO_3)_2.6H_2O$, and 1.81 g $(NH_4)_6Mo_7O_{27}.4H_2O$. The sample was dried at 125° C. for 4 hours and then treated with two equal portions of a solution consisting of 2.0 g $CsNO_3$ in 26 ml $H_2O$. The sample was dried for 4 hours at 125° C. after the first addition and overnight at 125° C. after the second addition. The sample was then treated with 13 ml of $H_2O$ containing 0.99 g $MnCl_2.4H_2O$ and again dried at 125° C. Finally, the sample was treated with 8 ml acetone containing 5.64 g $SnCl_2.2H_2O$ and dried at 125° C. The resulting catalyst had a composition which can be represented as 90 weight percent $CsCu_{0.2}Zn_{0.5}Mn_{0.5}MoO_x$/10 weight percent $Sn/Al_2O_3$.

Example 3

A 44 g sample of $\gamma$-$Al_2O_3$ was treated with 13 ml $H_2O$ containing 0.3 g $AgNO_3$, 1.93 g $Cu(NO_3)_2.3H_2O$, and 2.33 g $Ni(NO_3)_2.6H_2O$ and dried for 4 hours at 125° C. The dried sample was then treated with 6.3 g 91.96 weight percent $WO_3$ (as the ammonium salt) and dried overnight at 125° C. The resulting catalyst had a composition which may be represented as $Ag_{0.1}Cu_{0.45}Ni_{0.45}WO_x/Al_2O_3$ (10 weight percent W).

Example 4

A 10 g sample of $\gamma$-$Al_2O_3$ was impregnated with an aqueous solution containing 1.2 g $Ni(NO_3)_2.6H_2O$ and

Reaction of Carbon Monoxide and Hydrogen Sulfide

The following procedure was used to prepare the catalyst of the Example 12 in Table II and is illustrative of the procedure used to prepare all the catalysts reported in the Table.

A high surface area gamma-alumina extrudate (30 g, surface area of about 200 m$^2$/g, pellet form) was treated at 600° C. under nitrogen for several hours. The alumina was commercially obtained from Strem Chemicals. A mixture of copper nitrate, $Cu(NO_3).3H_2O$ (0.5 g); zinc nitrate, $Zn(NO_3)_2.6H_2O$ (1.5 g); ammonium heptamolybdate, $(NH_4)_6Mo_7O_{27}.4H_2O$ (1.81 g); and distilled water (13 cc) was then poured over the pellets and stirred well until all the liquid was absorbed. The pellets were then dried for approximately 4 hours at 125° C. A 26 cc solution of cesium nitrate, $Cs(NO_3)$(2.0 g), was then divided into two equal parts and the first part poured over the dried pellets and stirred well until all the liquid was absorbed. The pellets were then dried overnight at 125° C. in an oven. The next day this procedure was repeated with the remaining 13 cc of the cesium nitrate solution except that the pellets were then dried for only about 4 hours at 125° C. Subsequently, a solution of 1 g of manganese chloride, $MnCl_2.4H_2O$, dissolved in water (13 cc) was poured over the dried pellets and stirred well until all the liquid was absorbed. The wet pellets were again dried overnight at 125° C. Finally, a solution of stannous chloride, $SnCl_2.2H_2O$ (5.64 g), dissolved in acetone (18 cc) was poured over the dried pellets, stirred well until liquid was absorbed and then the pellets were dried for about 2 hours at 125° C.

Approximately 20 cc of the resulting catalyst precursor (gamma-alumina pellets impregnated with the various metal components) was then placed in a quartz tube (0.5" internal diameter, catalyst bed about 12" long) and held in place with quartz wool plugs. The precursor was then treated for about 15 minutes at room temperature with nitrogen, subsequently for about one hour at 400° C. with nitrogen and finally for about one hour at 400° C. with hydrogen sulfide. The resulting catalyst can be represented by the empirical formula $$CsCu_{0.2}Zn_{0.5}Mn_{0.5}Sn_{2.4}MoO_xS_y \qquad (II)$$

Procedure and Conditions

Unless otherwise noted, the reactions were conducted in the quartz tube used to condition and sulfide the catalyst precursor as described in the preceding paragraph. Following this pretreatment, a feed of hydrogen sulfide:carbon monoxide was introduced into the tube at a 1:1 molar ratio and at a flow rate that established a 10 second contact time of reactants over the catalyst bed. The off-gas rate was measured with a soap-film meter and the off-gas composition was determined after one hour of on-stream activity with the aid of a Carle 111 gas chromatograph equipped with a 158-b column system. Reject gases were scrubbed in a monoethanolamine/water solution and then vented to the hood. The reaction temperature of each example was approximately 400° C. and the tube was heated by means of a Lindberg tube furnace. The reactant gases were introduced into the tube from tanks through stainless steel tubing, regulators, flow controllers, and rotometers. The gases were purchased from the Matheson Gas Company and used without further purification.

The percent conversion as reported in the Table was calculated by subtracting the amount of hydrogen sulfide leaving the reactor from the amount of hydrogen sulfide fed to the reactor and dividing the difference by the amount of hydrogen sulfide fed to the reactor and then multiplying the quotient by 100. The ratios of hydrogen to methane and hydrogen to carbon dioxide were calculated by simply dividing the hydrogen recovered (in mole percent) by either the methane or carbon dioxide recovered (also in mole percent) and reporting the quotient. The higher the quotient, the better the selectivity. Although not reported in the Table, for each mole of hydrogen produced, one mole of carbonyl sulfide was also produced.

TABLE II

| | REACTION OF HYDROGEN SULFIDE AND CARBON MONOXIDE IN THE PRESENCE OF VARIOUS METAL OXIDES/SULFIDE CATALYSTS | | | |
|---|---|---|---|---|
| Example | Catalyst | H$_2$S Conversion (%) | H$_2$/CH$_4$ | H$_2$/CO$_2$ |
| 12 | Cs$_1$Cu$_{.2}$Zn$_{.5}$Mn$_{.5}$MoO$_x$S$_y$+ 10 w % Sn | 23.8 | 30 | 4 |
| 13 | Cs$_1$Cu$_{.2}$Zn$_{.5}$Mn$_{.5}$WO$_x$S$_y$ | 23.3 | 24.4 | 3.7 |
| 14 | Cs$_1$Cu$_{.2}$Zn$_{.5}$WO$_x$S$_y$ | 22.8 | 35.7 | 3.9 |
| 15 | Cs$_1$Cu$_{.2}$Zn$_{.5}$MoO$_x$S$_y$ | 24 | 2.5 | 1.1 |
| 16 | Cs$_1$Co$_{.25}$MoO$_x$S$_y$ | 24.64 | 1.30 | 0.65 |

Reaction of Carbonyl Sulfide and Oxygen

Examples 17–29

These Examples describe the oxidation of carbonyl sulfide over various bed packings. In each case, the bed packing occupied about 10 cc of a 12" quartz tube and O$_2$ was introduced as air. The carbonyl sulfide/oxygen feed were introduced into the tube such that the feed was in contact with the bed material approximately 10 seconds. The molar feed ratio and temperature along with the carbonyl sulfide conversion and molar product ratio are reported in Table III.

TABLE III

| | OXIDATION OF COS OVER VARIOUS BED PACKINGS | | | | |
|---|---|---|---|---|---|
| Example | Bed Packing | Temp. (°C.) | COS/O2 (Mole) | COS Conv. % | CO/CO2 (Mole) |
| 17 | γ-alumina* (extrudates) | 350 | 1 | 83 | 2.7 |
| 18 | glass beads* (3 mm dia.) | 400 | 1.4 | 56 | 16.5 |
| | (5 mm dia.) | 350 | 1.0 | 76 | 6.9 |
| 19 | glass wool* | 400 | 1.4 | 56 | 9.1 |
| 20 | quartz wool* | 400 | 1.4 | 51 | 7.5 |
| 21 | stainless steel wool* | 400 | 1.4 | 62 | 9.5 |
| 22 | SiO$_2$* (granular) | 400 | 1.4 | 52 | 8.0 |
| 23 | SiO$_2$/(CH$_3$)$_2$SiCl$_2$** (granular) | 350 | 1.4 | 8 | 2.3 |
| 24 | Porcelain* (1/4" saddles) | 350 | 1.4 | 53 | 9.8 |
| 25 | V$_1$S$_{1.2}$O$_x$ (coated on silica-alumina spheres to 13 wt %) | 350 | 1 | 91 | 1.4 |
| 26 | V$_1$P$_{1.2}$O$_x$ (coated on silica-alumina spheres to 14 wt %) | 400 | 1 | 92 | 4.1 |
| 27 | H$_3$Mo$_{12}$PO$_x$ (impregnated into γ-alumina extrudates to 10 wt %) | 300 | 1 | 78 | 0.27 |
| 28 | B$_2$O$_3$#(grand pellets) | 350 | 1 | 74 | 7.3 |
| 29 | CoCl$_2$ (impregnated into -alumina extrudates to 10 wt %) | 300 | 1 | 16 | 0.71 |

*Purchased.
**SiO$_2$ silylated with dimethyl dichlorosilane (5 wt % in toluene for 1 hour and at room temperature Reaction of Carbonyl Sulfide and Hydrogen The Examples 30–37 demonstrate the manufacture of various organic compounds from carbonyl sulfide and hydrogen. The procedure of these examples was essentially the same as that used in Examples 17-29. The conditions and results are reported in Tables VI-VIII.

TABLE IV
METHANE FROM $H_2$ AND COS

| | |
|---|---|
| Reaction Temperature | 300° C. |
| Reaction Pressure | Atmospheric |
| Contact Time | 3 seconds |
| COS:$H_2$:Air Mole Ratio | 1:4:19 |
| COS Conversion | 100 percent |
| Catalyst Time On-Stream | 25 minutes |

| Example | Catalyst | Methane (%) |
|---|---|---|
| 30 | 10 wt % NiO on $ZrSiO_4$ | 96.6 |
| 31 | 25 wt % NiO on $CeO_2$ | 95.1 |
| 32 | 10 wt % NiO on $SiO_2$ | 100 |
| 33 | 20 wt % NiO on $Al_2O_3$ | 97.1 |

TABLE V
METHYL MERCAPTAN FROM $H_2$ AND COS*

| | |
|---|---|
| Reaction Temperature | 300° C. |
| Reaction Pressure | 50 Atmospheres |
| COS Conversion | 100% |

| Ex. | Catalyst | Catalyst Time On-Stream (min) | Contact Time (sec) | COS:$H_2$:Air (Mole Ratio) | $CH_3SH$ (%) |
|---|---|---|---|---|---|
| 34 | 10 wt % NiO on $ZrSiO_4$ | 30 | 20 | 1:4:6.5 | 21.1 |
| 35 | 12.5 wt % NiO on $ZrO_2$ | 25 | 9 | 1:4:19 | 17.7 |
| 36 | 25 wt % NiO on $CeO_2$ | 75 | 9 | 1:2:19 | 22.4 |

*Significant amount of CO in product gas as well as minor amounts of such compounds as $CO_2$, $CH_3$—S—$CH_3$, etc.

TABLE VI
**$C_3$ HYDROCARBONS* FROM $H_2$ AND COS****

| | |
|---|---|
| Reaction Temperature | 300° C. |
| Reaction Pressure | Atmospheric |
| Contact Time | 3 seconds |
| COS:$H_2$:Air Mole Ratio | 1:4:19 |
| COS Conversion | 100% |
| Catalyst | 25 wt % NiO on $ZrO_2$ |

| Ex. | Catalyst Time On-Stream (min) | $C_3$ (%) |
|---|---|---|
| 37(a) | 120 | 8.9 |
| 27(b) | 180 | 11.8 |
| 37(c) | 240 | 9.3 |

*Propylene and/or propane.
**Significant amounts of $CH_4$, CO and $CO_2$ in product gas.

Although the invention has been described in considerable detail through the preceding examples, these examples are provided for the purpose of illustration. Many variations and modifications can be made by one skilled in the art without departing from the spirit and scope of this invention as described in the appended claims.

What is claimed is:

1. A process of reducing carbon oxides with hydrogen sulfide, the method comprising:
   (a) contacting at least one of carbon monoxide and carbon dioxide with hydrogen sulfide to form carbonyl sulfide,
   (b) contacting the carbonyl sulfide produced in (a) with oxygen to form carbon monoxide and sulfur dioxide, and
   (c) hydrogenating at least one of the carbon monoxide and carbonyl sulfide to an organic compound.

2. The process of claim 1 where the carbon oxide of step (a) is carbon monoxide and in step (c), carbon monoxide is hydrogenated to an alkane, alkene, alkanol or alkanethiol.

3. The process of claim 1 where the carbon oxide in step (a) is carbon monoxide and in step (c), carbonyl sulfide is hydrogenated to an alkane, alkene, alkanol or alkanethiol.

4. The process of claim 1 where in step (a) the carbon oxide is carbon dioxide, between steps (b) and (c) an intermediate step is conducted reacting the carbon monoxide from step (b) with hydrogen sulfide to form carbonyl sulfide and hydrogen, and carbon monoxide is hydrogenated in step (c) to form an alkane, alkene, alkanol or alkanethiol.

5. The process of claim 1 where in step (a) the carbon oxide is carbon dioxide, an intermediate step is conducted between steps (b) and (c) where the carbon monoxide formed in step (b) is reacted with hydrogen sulfide to produce carbonyl sulfide and hydrogen, and in step (c) carbonyl sulfide is hydrogenated to an alkane, alkene, alkanol or alkanethiol.

6. The process of claim 1 where in step (a) both carbon dioxide and carbon monoxide are contacted with hydrogen sulfide and in step (c) carbon monoxide is hydrogenated to an alkane, alkene, alkanol or alkanethiol.

7. The process of claim 1 where in step (a) both carbon dioxide and carbon monoxide are contacted with hydrogen sulfide and in step (c) carbonyl sulfide is hydrogenated to an alkane, alkene, alkanol or alkanethiol.

8. The process of claim 2 where step (a) is conducted in the vapor phase at a temperature between about 200-600 C. and at a pressure between about 0-1,000 psig.

9. The process of claim 3 where step (a) is conducted in the vapor phase at a temperature between about 200-600 C. and at a pressure between about 0-1,000 psig.

10. The process of claim 4 where in step (a) is conducted in the vapor phase at a temperature between about 20-800 C. and at a pressure between about 0-3,000 psig.

11. The process of claim 5 where step (a) is conducted in the vapor phase at a temperature between about 20-800 C. and at a pressure between about 0-3,000 psig.

12. The process of claim 8 where step (b) is conducted in the vapor phase at a temperature between about 200-500 C. and at a pressure between about 0-1,000 psig.

13. The process of claim 9 where step (b) is conducted in the vapor phase at a temperature between about 200-500 C. and at a pressure between about 0-1,000 psig.

14. The process of claim 10 where step (b) is conducted in the vapor phase at a temperature between about 200-500 C. and at a pressure between about 1-1,000 psig.

15. The process of claim 11 where step (b) is conducted in the vapor phase at a temperature between about 200-500 C. and at a pressure between about 0-1,000 psig.

16. The process of claim 6 where step (a) is conducted in the vapor phase at a temperature between about 200-500 C. and at a pressure between about 0-1,000 psig.

17. The process of claim 7 where step (a) is conducted in the vapor phase at a temperature between about 200–500 C. and at a pressure between about 0–1,000 psig.

18. The process of claim 15 where in step (c), carbon monoxide is hydrogenated to produce at least one of methanol, methane and propylene.

19. The process of claim 16 where in step (c), carbonyl sulfide is hydrogenated to produce at least one of methyl mercaptan, methane and propylene.

20. The process of claim 1 where in step (c) carbon monoxide is hydrogenated to produce at least one of methanol, methane and propylene.

21. The process of claim 1 where in step (c) carbonyl sulfide is hydrogenated to produce at least one of methyl mercaptan, methane and propylene.

* * * * *